(12) United States Patent
Srinivasan et al.

(10) Patent No.: US 9,109,006 B2
(45) Date of Patent: Aug. 18, 2015

(54) GLATIRAMER ACETATE MOLECULAR WEIGHT MARKERS

(76) Inventors: Santhanakrishnan Srinivasan, Tuticorin (IN); Karthik Ramasamy, Andhra Pradesh (IN); Chakravarthula Kalyan Narasimham Nallam, Andhra Pradesh (IN); Yagna Kiran Kumar Komaravolu, Andhra Pradesh (IN); Sudheer Reddy Kallam, Andhra Pradesh (IN); Bala Harsha Vardhan Ganji, Andhra Pradesh (IN); Ravindra Chary Bathoju, Andhra Pradesh (IN); Basanthi Devi, Andhra Pradesh (IN)

( * ) Notice: Subject to any disclaimer, the term of this patent is extended or adjusted under 35 U.S.C. 154(b) by 262 days.

(21) Appl. No.: 13/812,684

(22) PCT Filed: Jul. 28, 2011

(86) PCT No.: PCT/US2011/045724
§ 371 (c)(1),
(2), (4) Date: Mar. 5, 2013

(87) PCT Pub. No.: WO2012/016042
PCT Pub. Date: Feb. 2, 2012

(65) Prior Publication Data
US 2013/0205877 A1 Aug. 15, 2013

Related U.S. Application Data

(60) Provisional application No. 61/389,360, filed on Oct. 4, 2010.

(30) Foreign Application Priority Data

Jul. 29, 2010 (IN) ............................ 2146/CHE/2010

(51) Int. Cl.
*G01N 33/68* (2006.01)
*G01N 30/06* (2006.01)
*C07K 2/00* (2006.01)
*B01D 15/34* (2006.01)
*G01N 30/02* (2006.01)

(52) U.S. Cl.
CPC . *C07K 2/00* (2013.01); *B01D 15/34* (2013.01); *G01N 30/02* (2013.01); *Y10T 436/105831* (2015.01); *Y10T 436/255* (2015.01)

(58) Field of Classification Search
CPC .......... B01D 15/34; C07K 2/00; G01N 30/02; Y10T 436/10; Y10T 436/105831; Y10T 436/109163; Y10T 436/25; Y10T 436/25375; Y10T 436/255
USPC ............. 436/8, 15, 19, 86, 89, 161, 174, 177, 436/178; 422/68.1, 70, 535; 424/499; 73/61.52, 61.55; 530/300, 344; 210/635, 198.2
See application file for complete search history.

(56) References Cited

U.S. PATENT DOCUMENTS

| | | | |
|---|---|---|---|
| 5,800,808 A | 9/1998 | Konfino et al. | |
| 6,514,938 B1 | 2/2003 | Gad et al. | |
| 7,163,802 B2 | 1/2007 | Gad et al. | |
| 2003/0157720 A1 | 8/2003 | Li | |
| 2005/0256046 A1* | 11/2005 | Gad et al. | 514/12 |
| 2006/0122113 A1* | 6/2006 | Pinchasi et al. | 514/12 |
| 2006/0154862 A1* | 7/2006 | Ray et al. | 514/12 |
| 2007/0059798 A1 | 3/2007 | Gad et al. | |
| 2009/0111133 A1 | 4/2009 | Gu et al. | |
| 2010/0285593 A1 | 11/2010 | Amoura | |
| 2013/0281663 A1* | 10/2013 | Kvs et al. | 530/330 |
| 2013/0323771 A1* | 12/2013 | Sathe et al. | 435/23 |

OTHER PUBLICATIONS

International Search Report dated Apr. 9, 2012 for corresponding International Patent Application No. PCT/US2011/045724.

* cited by examiner

*Primary Examiner* — Maureen Wallenhorst
(74) *Attorney, Agent, or Firm* — Pergament Gilman & Cepeda LLP; Milagros A. Cepeda; Edward D. Pergament

(57) ABSTRACT

Aspects of the present application relate to molecular weight markers of glatiramer acetate for accurate determination of the average molecular weight of glatiramer acetate.

14 Claims, 9 Drawing Sheets

GLATIRAMER ACETATE MOLECULAR WEIGHT MARKERS

This application is a National Stage Application under 35 U.S.C. 371 of PCT International Application No. PCT/US2011/045724, filed Jul. 28, 2011, which claims priority to claims the benefit of Indian Provisional Application 2146/CHE/2010, filed on Jul. 29, 2010 and U.S. Provisional Application No. 61/389,360, filed on Oct. 4, 2010, all of which are hereby incorporated by reference in their entirety.

Aspects of the present application relate to polypeptides having no predetermined amino acid sequence for use as molecular weight markers of glatiramer acetate and for the accurate determination of the average molecular weight of glatiramer acetate.

Glatiramer acetate (formerly known as copolymer-1) is chemically designated L-glutamic acid polymer with L-alanine, L-lysine, and L-tyrosine, acetate salt. It has the structural formula of Formula (I).

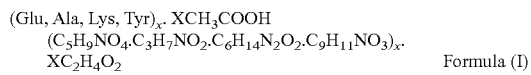

$(C_5H_9NO_4.C_3H_7NO_2.C_6H_{14}N_2O_2.C_9H_{11}NO_3)_x.$
$XC_2H_4O_2$  Formula (I)

Glatiramer acetate is the acetate salt of a synthetic mixture of polypeptides, each of which consists essentially of the four naturally occurring amino acids: L-glutamic acid, L-alanine, L-tyrosine, and L-lysine with an average molar fraction of 0.141, 0.427, 0.095, and 0.338, respectively. The average molecular weight of glatiramer acetate is 5,000-9,000 Daltons. Glatiramer acetate is sold in USA as Copaxone®, a registered trademark of Teva Pharmaceutical Industries Ltd. Glatiramer acetate is indicated for reduction of the frequency of relapses in patients with Relapsing-Remitting Multiple Sclerosis (RRMS).

U.S. Pat. No. 6,514,938 discloses seven polypeptides having an amino acid sequences which are identified in the patent. U.S. Pat. No. 7,074,580 discloses a process for obtaining a pharmaceutical product containing a mixture of polypeptides. Each of the polypeptides consists essentially of alanine, glutamic acid, tyrosine, and lysine. The mixture has an average molecular weight from 4000 to 13,000 Daltons and in the mixture the molar fraction of alanine is 0.427, of glutamic acid is 0.141, of lysine is 0.337, and of tyrosine is 0.093. The patent teaches determining the molecular weight distribution of a batch of an aqueous mixture of polypeptides, each of which consists essentially of alanine, glutamic acid, tyrosine, and lysine. The molecular weight distribution determination uses a gel permeation chromatography column to determine whether the mixture has an average molecular weight from 4000 to 13,000 Daltons for inclusion in a pharmaceutical product. The determination method comprises calibrating the molecular weight obtained using the gel permeation chromatography column by subjecting a plurality of molecular weight markers, each of which is a polypeptide consisting essentially of alanine, glutamic acid, tyrosine and lysine and having a predetermined amino acid sequence, to chromatography on the column to establish a relationship between retention time on the column and molecular weight.

U.S. Pat. No. 7,163,802 discloses in a process for obtaining a pharmaceutical product containing a mixture of polypeptides, each of which consists essentially of alanine, glutamic acid, tyrosine, and lysine. The mixture of polypeptides has an average molecular weight between 2000 and 40,000 Daltons and in the mixture the molar fraction of alanine is 0.38 to 0.5, of glutamic acid is 0.13 to 0.15, of tyrosine is 0.08 to 0.10 and of lysine is 0.3 to 0.4. During the process, a batch of a mixture of polypeptides, each of which consists essentially of alanine, glutamic acid, tyrosine, and lysine, is tested using a gel permeation chromatography column to determine whether the mixture has an average molecular weight between 2000 and 40,000 Daltons for inclusion in the pharmaceutical product. The testing method comprises calibrating the gel permeation chromatography column by subjecting a plurality of molecular weight markers, each of which is a polypeptide consisting essentially of alanine, glutamic acid, tyrosine and lysine and having a predetermined amino acid sequence, to chromatography on the column to establish a relationship between retention time on the column and molecular weight said relationship being used to determine average molecular weight of the mixture of polypeptides.

There remains a need to provide molecular weight markers of glatiramer acetate useful as standards for determining the peak average molecular weight of glatiramer acetate polypeptide compositions.

SUMMARY

The present application provides polypeptides having no predetermined amino acid sequence for use as molecular weight markers of glatiramer acetate, which are useful as standards for determining the peak average molecular weight of glatiramer acetate a polypeptide.

DETAILED DESCRIPTION

Figure 1:
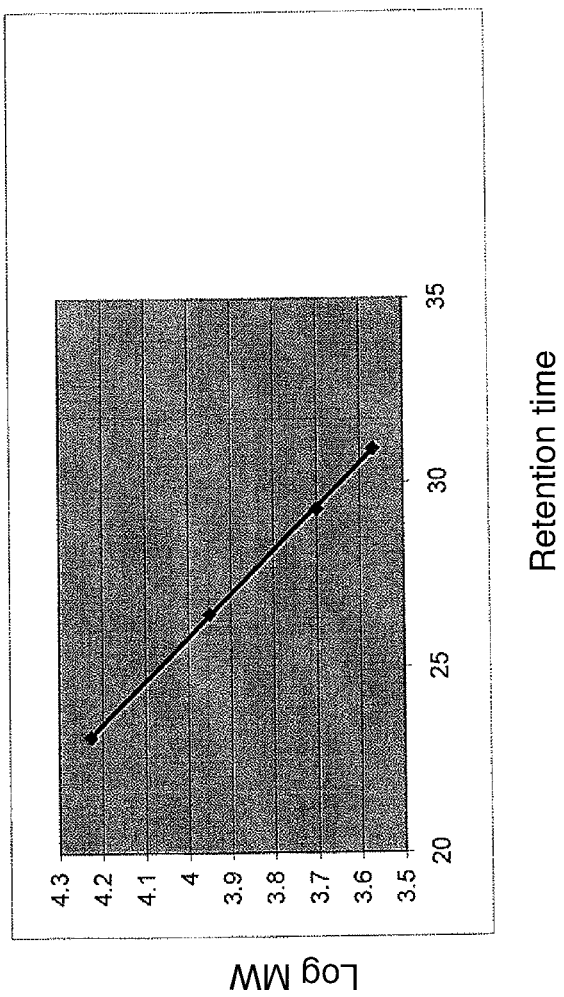
FIG. 1 is a plot of the retention time (RT) of the present molecular weight markers versus the log molecular weight of those markers, using the RT-based algorithm.
Figure 2:
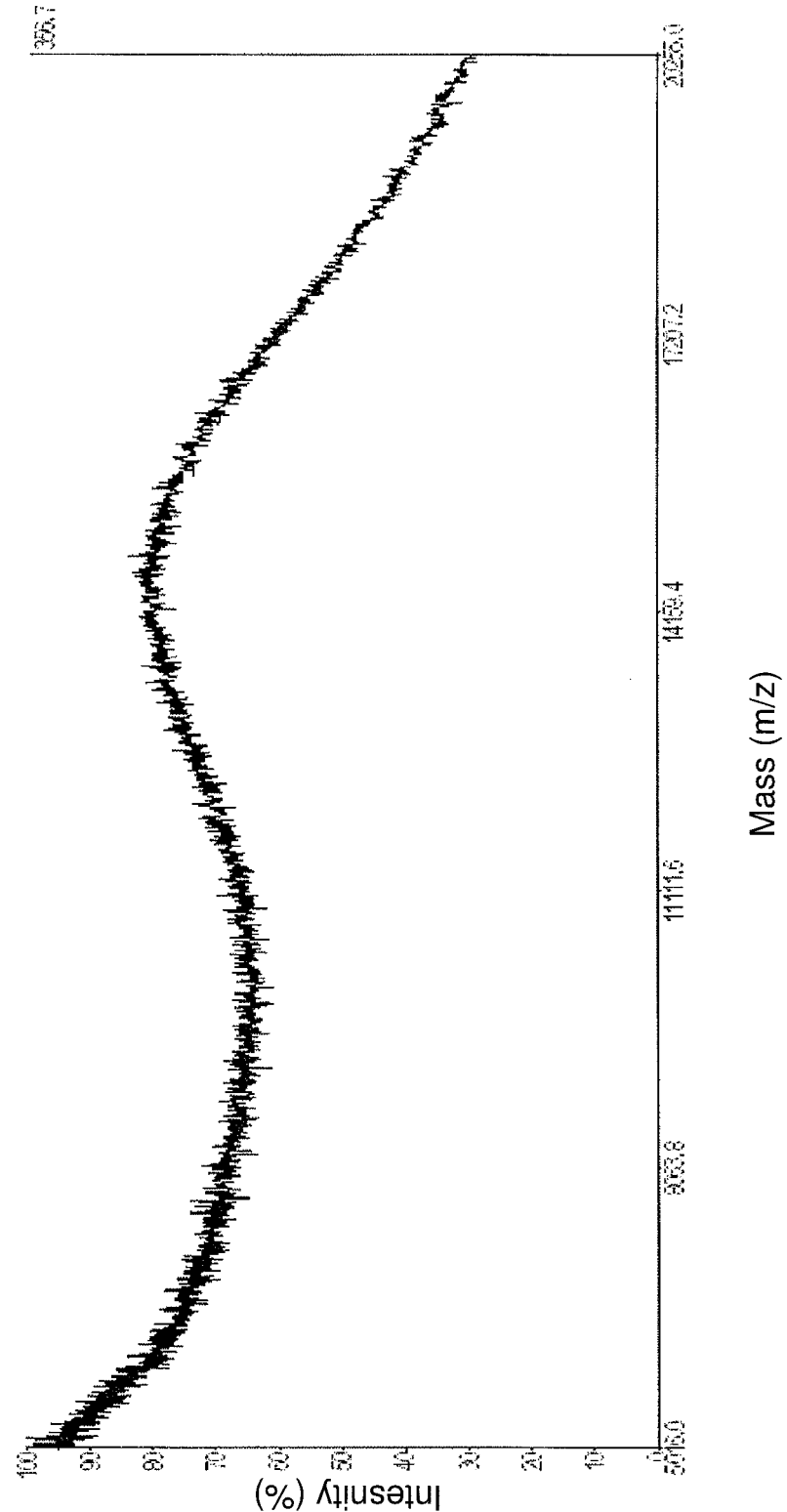
FIG. 2 is an illustration of MALDI spectrum of molecular weight marker 1 prepared according to Example 1.
Figure 3:
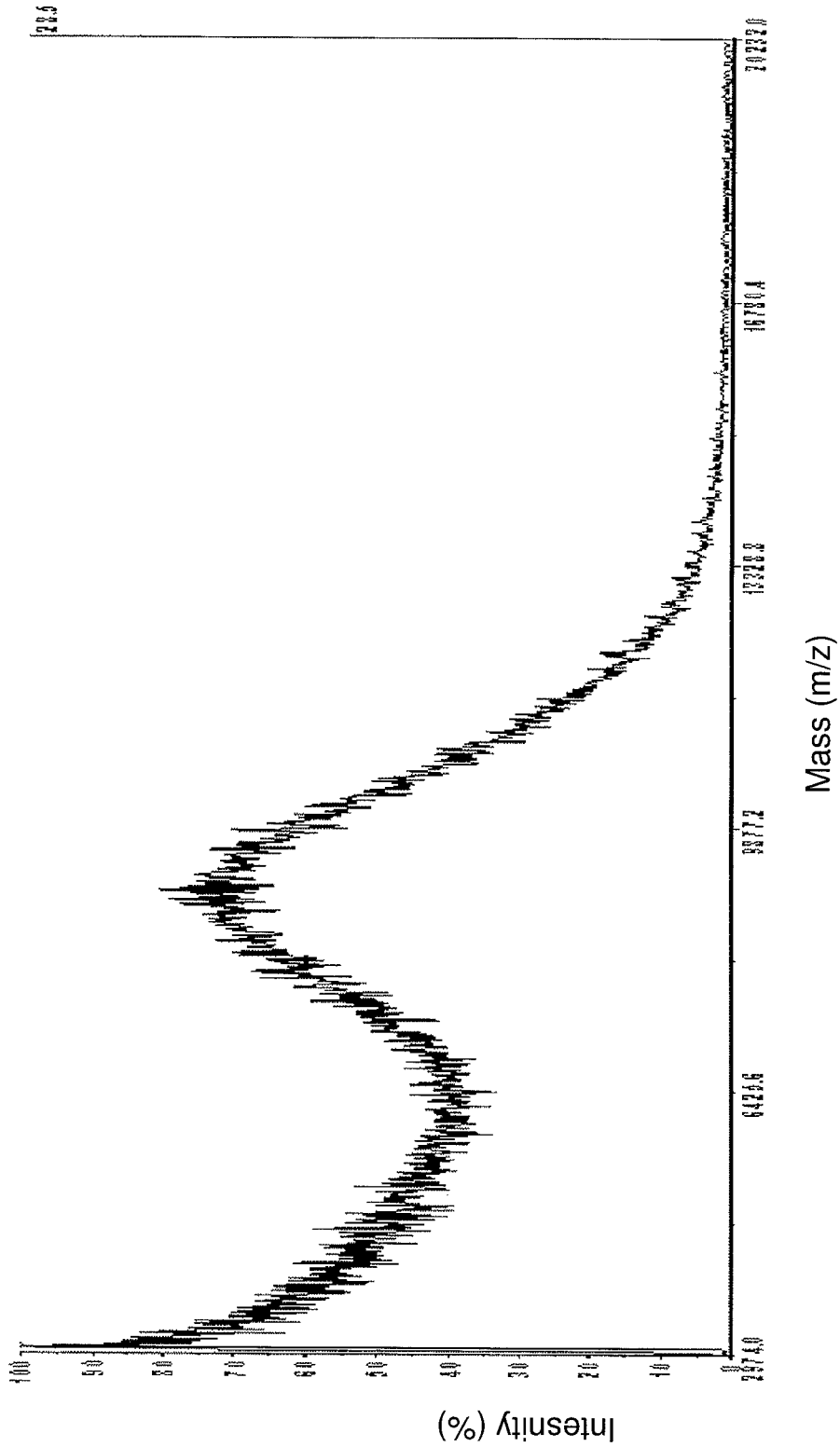
FIG. 3 is an illustration of MALDI spectrum of molecular weight marker 2 prepared according to Example 1.
Figure 4:
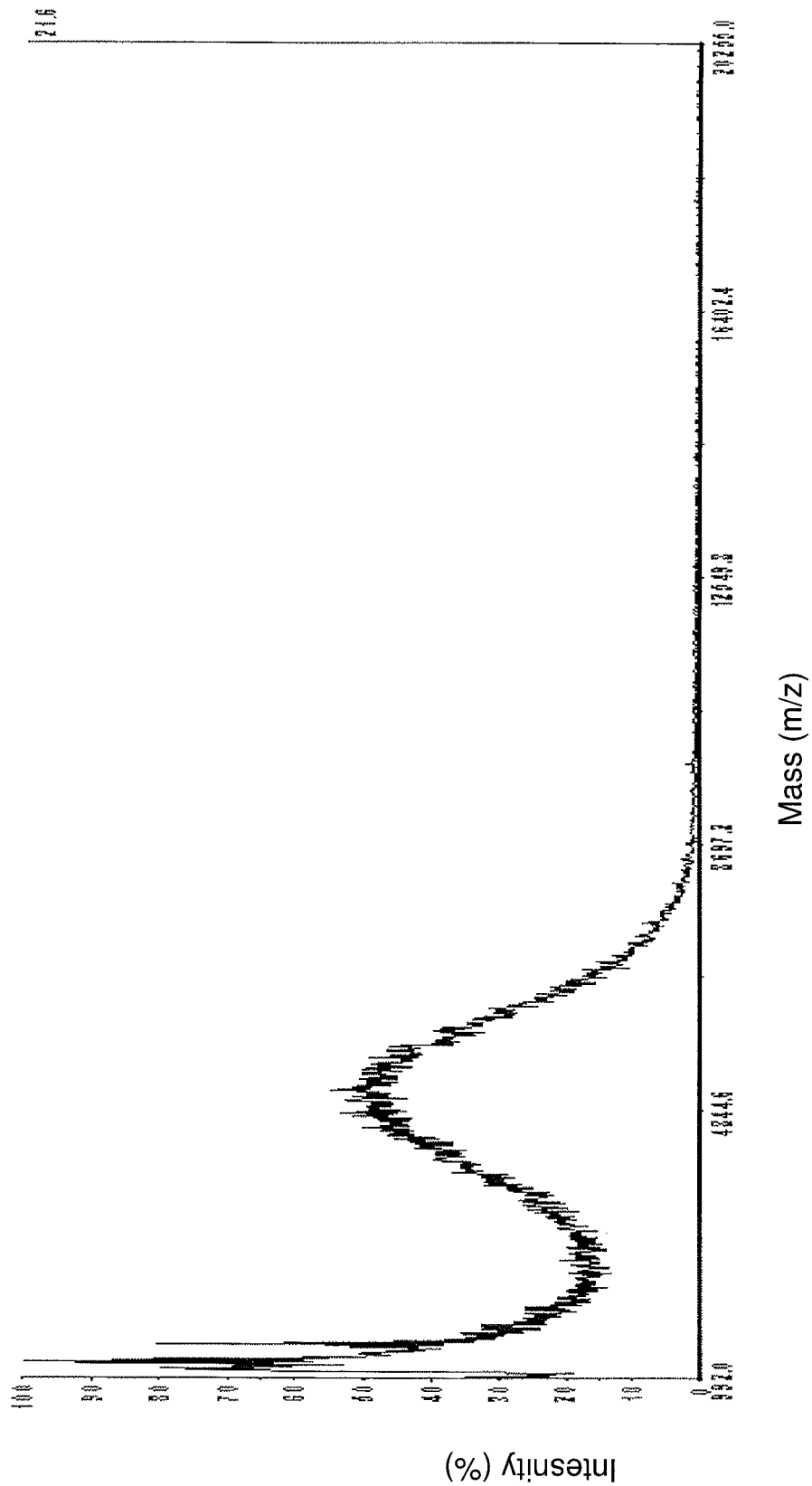
FIG. 4 is an illustration of MALDI spectrum of molecular weight marker 3 prepared according to Example 1.
Figure 5:
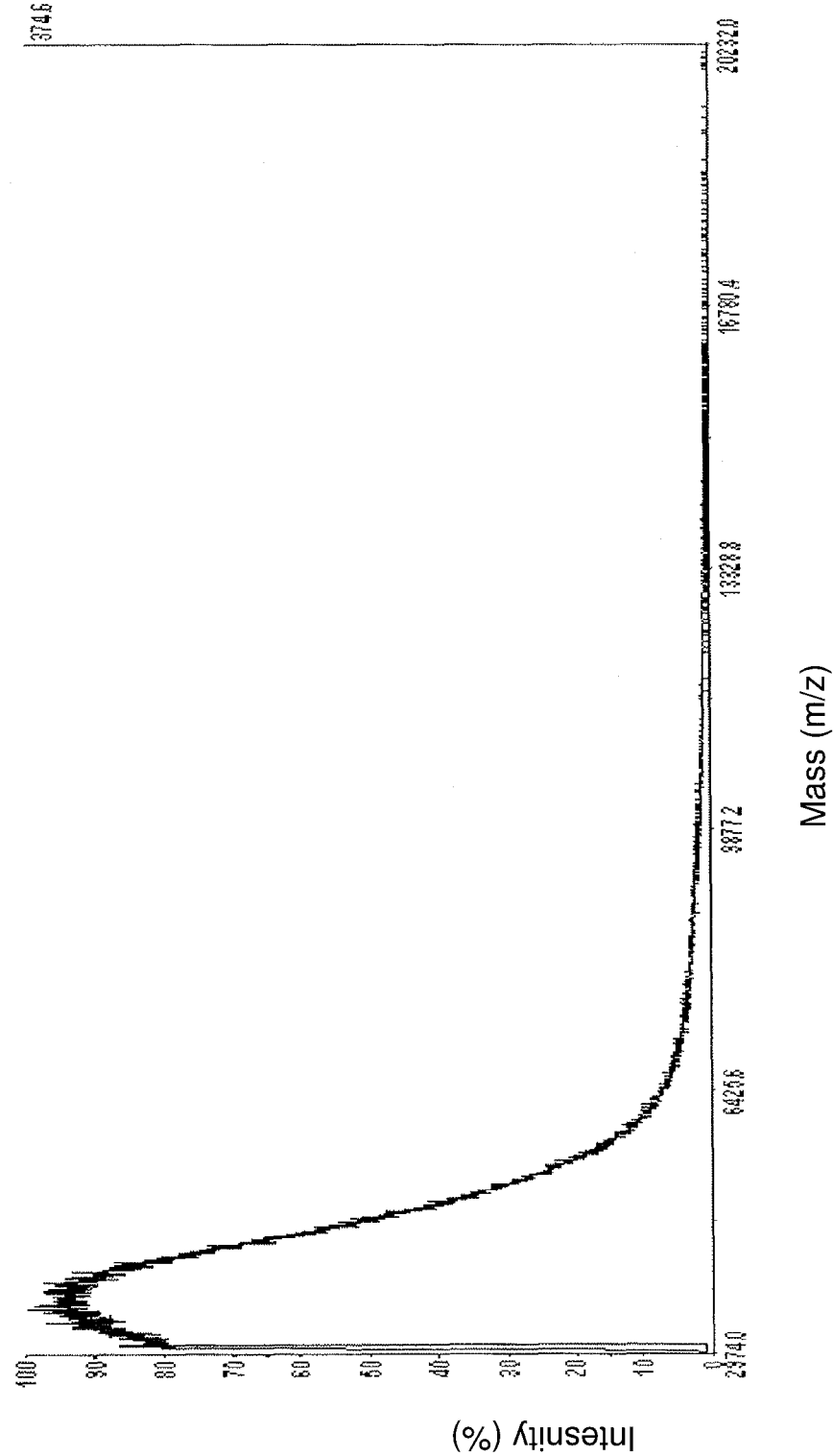
FIG. 5 is an illustration of MALDI spectrum of molecular weight marker 4 prepared according to Example 1.
Figure 6:
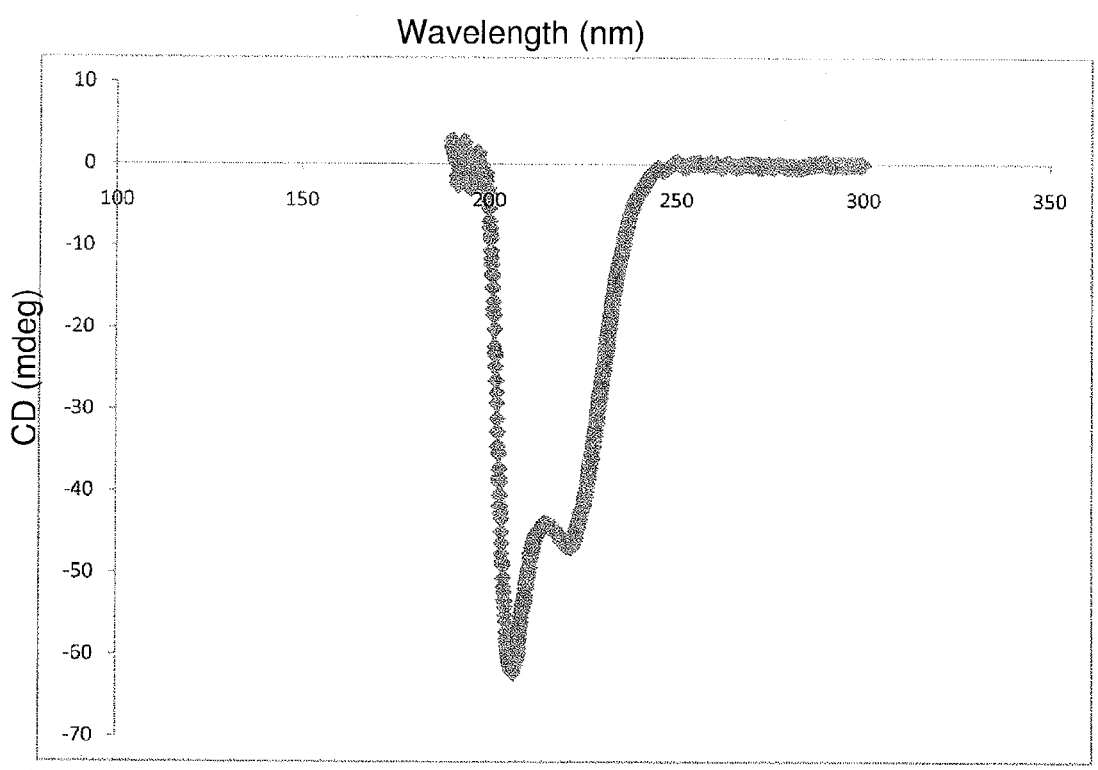
FIG. 6 is an illustration of circular dichroism spectrum of Copaxone®.
Figure 7:
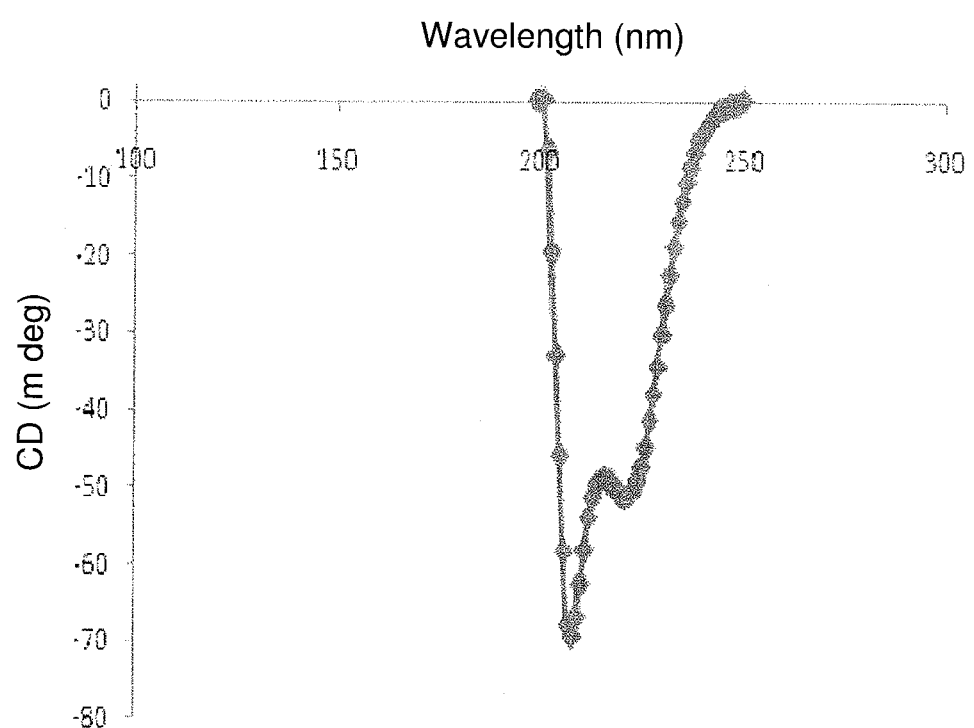
FIG. 7 is an illustration of circular dichroism spectrum of molecular weight marker 2 prepared according to Example 1.
Figure 8:
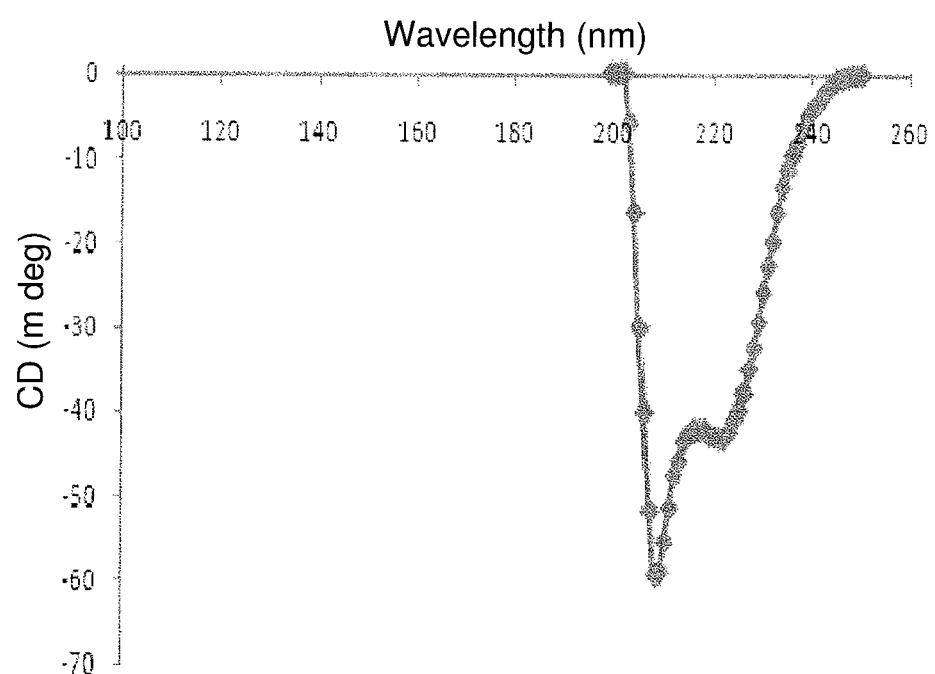
FIG. 8 is an illustration of circular dichroism spectrum of molecular weight marker 3 prepared according to Example 1.
Figure 9:
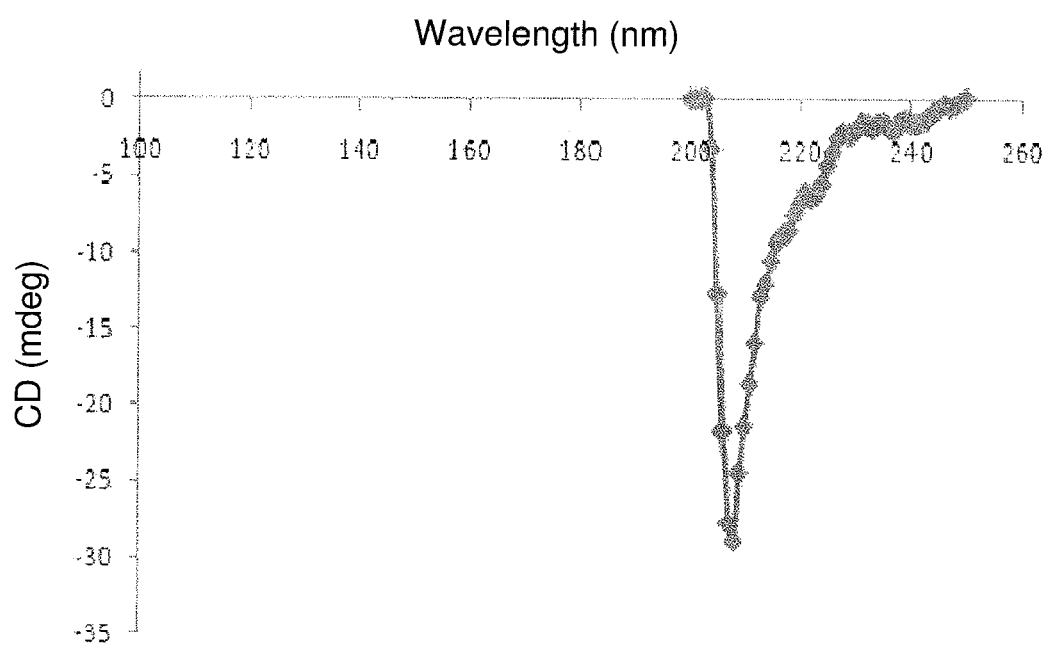
FIG. 9 is an illustration of circular dichroism spectrum of molecular weight marker 4 prepared according to Example 1.

The present application provides polypeptides having no predetermined amino acid sequence for use as molecular weight markers of glatiramer acetate , which are useful as standards for determining the peak average molecular weight of glatiramer acetate a polypeptide.

The present application provides polypeptides for use as molecular weight markers of glatiramer acetate for determining the peak average molecular weight of glatiramer acetate a polypeptide.

In an aspect, the present application provides polypeptides having an amino acid composition corresponding to glatiramer acetate polypeptide and an identified molecular weight which is between about 2,000 Daltons and about 40,000 Daltons or between about 2,000 Daltons and about 20,000 Daltons or between about 2,000 Daltons and about 15,000 Daltons or between about 2,000 Daltons and about 10,000

Daltons; for use as molecular weight markers for determining the average molecular weight of a polypeptide.

In an aspect, the present application provides polypeptides having an amino acid composition corresponding to glatiramer acetate and an identified molecular weight which is between about 2,000 Daltons and about 40,000 Daltons or between about 2,000 Daltons and about 20,000 Daltons or between about 2,000 Daltons and about 15,000 Daltons or between about 2,000 Daltons and about 10,000 Daltons; for use as molecular weight markers for determining the average molecular weight of glatiramer acetate.

In an aspect, the present application provides polypeptides consisting essentially of amino acids alanine, glutamic acid, tyrosine, and lysine in molar fractions of from about 0.38 to about 0.50 alanine, from about 0.13 to about 0.155 glutamic acid, from about 0.08 to about 0.12 tyrosine, and from about 0.28 to about 0.4 lysine, for use as molecular weight markers for determining the average molecular weight of a polypeptide.

In an aspect, the present application provides polypeptides consisting essentially of amino acids alanine, glutamic acid, tyrosine, and lysine in molar fractions of from about 0.38 alanine to about 0.50 alanine, from about 0.13 glutamic acid to about 0.155 glutamic acid, from about 0.08 tyrosine to about 0.12 tyrosine, and from about 0.28 lysine to about 0.4 lysine, for use as molecular weight markers for determining the average molecular weight of glatiramer acetate.

In an aspect, the present application provides processes for preparing molecular weight markers of the present application, which includes one or more of the following steps, individually or in the sequence recited:
(a) fractionating the glatiramer acetate polypeptide in a gel permeation chromatography (GPC) column;
(b) passing the fractions collected in step (a) through molecular weight cut-off membranes; and
(c) isolating the molecular weight markers by lyophilizing the fractions collected from step (b).

In an aspect, the present application provides processes for preparing molecular weight markers of the present application, which includes one or more of the following steps, individually or in the sequence recited:
(a) fractionating the glatiramer acetate in a gel permeation chromatography (GPC) column;
(b) passing the fractions collected in step (a) through molecular weight cut-off membranes; and
(c) isolating the molecular weight markers by lyophilizing the fractions collected from step (b).

Step (a) involves fractionating a sample of glatiramer acetate in a gel permeation chromatography (GPC) column. Suitable chromatography media for gel filtration that may be used in step (a) include, but are not limited to, Superdex™, Sephacryl™, Superose™ and Sephadex™, and the like. Superdex™ is a composite medium based on highly cross-linked porous agarose particles to which dextran have been covalently bonded. Superdex™ is a trademark of GE Healthcare companies. Sephacryl™ is an allyl dextran cross-linked with N, N'-methylene bisacrylamide. Sephacryl™ is a trademark of GE Healthcare. Superose™ is a medium with high physical and chemical stability based on highly cross-linked porous agarose particles. Superose™ is a trademark of GE Healthcare Ltd, a General Electric Company. Sephadex™ is dextran cross-linked with epichlorohydrin. Sephadex™ is a trademark of GE Healthcare companies.

A sample of glatiramer acetate may be prepared by dissolving in a suitable solvent and then the resultant solution is filtered to remove any unwanted particulate matter through syringe filters. Suitable solvent that may be used for the preparation of a sample of glatiramer acetate include, but are not limited to, Milli Q® water, and the like. is a registered trademark of the Millipore Corporation, Billerica, Mass.

Suitable buffers that may be used in step (a) include, but are not limited to, acetate buffers, phosphate buffers, citrate buffers, and sodium chloride, or mixtures thereof.

Step (b) involves passing of the fractions collected in step (a) through molecular cut-off membranes for obtaining the markers with a narrow molecular weight distribution. Suitable molecular cut-off membranes that may be used in step (b) may range from 1 KDa to 10 KDa, or 1 KDa to 20 KDa, or 1 KDa to 30 KDa.

Step (b) may be preceded by an optional lyophilization of the individual fractions collected in step (a), dissolving the lyophilizates in a solvent, and then passing through molecular cut-off membranes.

Step (c) involves isolation of molecular weight markers by lyophilizing the fractions collected from step (b).

The molecular weights of the markers of the present application may be determined by any method including the methods described in the art. For example molecular weight of markers of present application may be determined by Matrix-Assisted Laser Desorption/Ionization (MALDI) or Low Angle Laser Light Scattering Detection (LALLS) or Multi Angle Light Scattering Detection (MALLS).

Glatiramer acetate that is used as the input for the process of the present application may be obtained by any process including the processes described in the art. For example glatiramer acetate may be prepared by the processes described in International Application No. PCT/U.S. Ser. No. 11/34102.

In an aspect, the present application provides a method for determining the peak average molecular weight of a polypeptide or a pharmaceutically acceptable salt thereof, which comprises subjecting the polypeptide or a pharmaceutically acceptable salt thereof to chromatography on a chromatographic column so as to determine the average molecular weight of the polypeptide or a pharmaceutically acceptable salt thereof, wherein the chromatographic column is calibrated by using a plurality of molecular weight markers of the present application, wherein each of the molecular weight marker is a polypeptide having no predetermined amino acid sequence.

In an aspect, the present application provides a method for determining the peak average molecular weight of glatiramer acetate or a pharmaceutically acceptable salt thereof, which comprises subjecting the glatiramer acetate or a pharmaceutically acceptable salt thereof to chromatography on a chromatographic column so as to determine the peak average molecular weight of the glatiramer acetate or a pharmaceutically acceptable salt thereof, wherein the chromatographic column is calibrated by using a plurality of molecular weight markers of the present application, wherein each of the molecular weight markers is a polypeptide having no predetermined amino acid sequence.

In another aspect, the present application provides a process of calibration of gel permeation chromatography column by using molecular weight markers of the present application.

In an aspect, the present application provides a plurality of molecular weight markers for determining the average molecular weight of a polypeptide on a molecular weight fractionation column.

In an aspect, the present application provides a plurality of molecular weight markers for determining the average molecular weight of glatiramer acetate on a molecular weight fractionation column.

In another aspect, the present application provides a linear relationship between the log molecular weight of the glatiramer acetate molecular weight markers of the present application and the retention time of the molecular weight markers on a molecular weight fractionation column.

To certify a polypeptide e.g., copolymer 1 (glatiramer acetate preparation for use in a pharmaceutical product, it is necessary to accurately determine the average molecular weight of the polypeptides in the preparation. Molecular weight markers that have chemical and physical characteristics similar to polypeptide provide an accurate and robust calibration set for determination of molecular weights of production batches. The present application provides derivatives of polypeptide e.g., glatiramer acetate useful as molecular weight markers for determining the average molecular weight of polypeptide e.g., glatiramer acetate preparations.

Molecular weight markers of the present application include polypeptides having an amino acid composition approximately corresponding to polypeptide e.g., glatiramer acetate, and an identified molecular weight which is between about 2,000 Daltons and about 40,000 Daltons, between about 2,000 Daltons and about 20,000 Daltons, between about 2,000 Daltons and about 15,000 Daltons, or between about 2,000 Daltons and about 10,000 Daltons; and are useful for accurately determining the average molecular weight of polypeptide e.g., glatiramer acetate. It follows from the requirement for an identified molecular weight that a molecular weight marker should not be highly polydispersed and should have a narrow molecular weight distribution. The molecular weight markers of the present application are not fixed sequence markers.

In an aspect, the present application provides molecular weight markers consisting essentially of amino acids alanine, glutamic acid, tyrosine, and lysine in defined molar ratios. The molar ratio of amino acids of molecular weight markers of present application is same as that found in a polypeptide e.g., glatiramer acetate.

Such a correspondence in molar ratios provides the best molecular weight markers because those markers will have a charge and a molecular shape which is similar to that of a polypeptide e.g., glatiramer acetate. When structurally dissimilar markers are used, the markers may migrate or elute somewhat differently from polypeptide e.g., glatiramer acetate copolymer preparations, though these preparations have the same molecular weight as that of markers.

The plurality of molecular weight markers are polypeptides. The plurality of markers can be two to about ten or more. Each of these polypeptides has an identified peak average molecular weight which is between about 2,000 Daltons and about 40,000 Daltons, between about 2,000 Daltons and about 20,000 Daltons, between about 2,000 Daltons and about 15,000 Daltons, or between about 2,000 Daltons and about 10,000 Daltons; and an amino acid composition which corresponds approximately to that of polypeptide e.g., glatiramer acetate.

When such a plurality of molecular weight markers of the present application are used as standards for determining the average molecular weight of a polypeptide e.g., glatiramer acetate, a relationship which is approximately linear exists between the retention time of the molecular weight markers of the present application on the chromatographic column and the log of the molecular weight of the markers. A plurality of markers is used which is sufficient to establish approximately the linear relationship between the retention time and the molecular weight.

The molecular weight markers of the present application may have therapeutic activity which is similar to glatiramer acetate polypeptide. These markers may be used in any molecular size discrimination system using any available molecular weight determination procedure or apparatus. For example, the present markers may be used for calibration of any chromatographic procedure or apparatus which is used for molecular weight determinations of polypeptides. Such a chromatographic apparatus may be a molecular weight sizing column which separates polypeptides on the basis of their molecular size.

Examples of molecular weight sizing columns include TSK-GEL® columns, Sephadex™ columns, Sepharose® columns, Sephacryl™ columns, and Superose™ columns.

DEFINITIONS

The following definitions are used in connection with the present invention unless the context indicates otherwise. Sephacryl® is a covalently cross linked dextran/bisacrylamide copolymer gel formed into beads. It is used in gel filtration columns for separating molecules in the size range 5 kD to 1.5 million Dalton. Sephacryl® S-100 has a 1 kD - 100 kD molecular weight range and has a particle size of 25 -75 μm. Sephacryl® is a registered trademark of GE Healthcare. Superose™ 12 is a cross-linked, agarose-based medium optimized for high performance gel filtration of biomolecules. It has an exclusion limit of ~2×10$^6$ $M_r$, and is a composite of cross-linked agarose with a bead diameter of 8-12 Superose™ is a trademark of GE Healthcare Ltd. TSK-GEL® is a registered trademark of Tosoh Corporation. Sepharose® is a registered trademark of GE Healthcare.

Certain specific aspects and embodiments of the present application will be explained in greater detail with reference to the following examples, which are provided only for purposes of illustration and should not be construed as limiting the scope of the application in any manner. Reasonable variations of the described procedures are intended to be within the scope of the present invention. While particular aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

EXAMPLES

Example 1

Preparation of Molecular Weight Markers of Glatiramer Acetate.

Matrix : Sephacryl™ S-100 HR (high resolution)
Bed volume : 320 mL
Elution mode : Isocratic
Flow rate : 1.8 mL/min
Wave length : 280 nm & 215 nm
Mobile phase: Phosphate buffer (mM), pH 7.2, 7.72 g of $NaH_2PO_4$, 20.45 g of $Na_2HPO_4$ with 35.05 g of NaCl (150 mM)/4 L water
Sample Preparation: glatiramer acetate (350 mg) is dissolved in Milli-Q® water (10 mL) and filtered through 0.45 μm syringe filter.

The column is stabilized with the above prepared mobile phase. The flow rate of the mobile phase is kept constant and stabilization is continued until base line reaches constant value. Sample is loaded on to the column at the same flow rate through pump B assembly. The set mark option is used to indicate injection marking. Absorbencies are recorded at dual wavelengths such as 215 nm & 280 nm. At nearly 111 mL of elution volume, the peak at 280 nm starts rising up. The fraction collector is activated to deliver 9 mL of each fraction. At 180 mL of elution volume the peak reaches its maximum value. Mobile phase flow still continues. At around 300 mL of elution volume, the peak almost reaches its baseline. Around 15 fractions are collected (9 mL of each volume), the fractionation is stopped. Of the collected fractions, one fraction from the rising peak, two near the peak apex and one at the tailing peak are chromatographed on Superose™ 12 column and the peak retention time for each of the fractions recorded. Each of these fractions elutes at a distinct retention time.

The same procedure was repeated for numerous batches and the selected fractions eluted at the same retention time in the Superose™-12 column when their elution time and elution volume during fractionation were constant. The collected fractions are lyophilized individually to give 80-90 mg each. The four selected fractions, at about RT 23.0 minutes, at about RT 26 minutes, at about RT 29 minutes and at about RT 30 minutes are then concentrated through a 10 KDa molecular weight cutoff membrane, a 3 KDa molecular weight cutoff membrane, a 3 KDa molecular weight cutoff membrane and a 3 KDa molecular weight cut off membrane respectively. The concentrated solutions are lyophilized individually to afford 15 mg, 30 mg, 35 mg, and 12 mg of the title compound.

Confirmation of molecular weight of the markers of the present application by MALDI (Matrix-Assisted Laser Desorption/Ionization) is given below:

| S. No. | Peak RT (Minutes) | Peak Average Molecular weight |
| --- | --- | --- |
| 1 | 23.124 | 16833 Daltons |
| 2 | 26.44 | 8908 Daltons |
| 3 | 29.281 | 5006 Daltons |
| 4 | 30.909 | 3709 Daltons |

Example 2

Preparation of Glatiramer Acetate Molecular Weight Markers.

Matrix : Sephacryl™ S-100 HR (high resolution)
Bed volume : 900 mL
Bed height : 460 mm
Elution mode : Isocratic
Flow rate : 4.8 mL/min
Wave length : 280 nm & 215 nm
Mobile phase: Phosphate buffer (mM), pH 7.2, 7.72 g of $NaH_2PO_4$, 20.45 g of $Na_2HPO_4$ with 11.688 g of NaCl/4 L water
Sample Preparation: glatiramer acetate (1500 mg) is dissolved in Milli-Q® water (10 mL) and filtered through 0.45 µm syringe filter.

The column is stabilized with the above prepared mobile phase. The flow rate of the mobile phase is kept constant and stabilization is continued until base line at absorbance @ 215 nm reaches constant value. Sample is loaded on to the column at the same flow rate through pump B assembly. The set mark option is used to indicate injection loading. Absorbencies are recorded at dual wavelengths such as 215 nm & 280 nm. At nearly 420 mL of elution volume, the peak at 215 nm starts rising up. The fraction collector is activated to deliver 10 mL of each fraction. At nearly 640 mL of elution volume the peak reaches its maximum value.

Mobile phase flow still continues. At around 1025 mL of elution volume, the peak almost reaches its baseline. The fractionation is stopped. Two consecutive fractions from the fraction collector are mixed together to get the required fraction volume of 20 mL each. After fractionation, the column is stabilized with mobile phase for the next cycle. The same procedure was repeated for numerous batches. Pooled fractions from the each batch were chromatographed on Superose™ 12 column and the peak retention time for each of the fractions recorded. Each of these fractions elutes at a distinct retention time as given in tables 1, 2, & 3 respectively. Fractions with similar retention time from different batches are pooled together for further processing.

TABLE 1

Batch No. 1

| Fraction No. | Retention time (minutes) |
| --- | --- |
| Fraction No. 1& 2 | Low response |
| Fraction No. 3& 4 | 24.737 |
| Fraction No. 7&8 | 26.330 |
| Fraction No. 11&12 | 27.995 |
| Fraction No. 15&16 | 29.596 |
| Fraction No. 19&20 | 31.171 |
| Fraction No. 23 & 24 | 33.028 |
| Fraction No. 27&28 | 36.271 |

TABLE 2

Batch No. 2

| Fraction No. | Retention time (minutes) |
| --- | --- |
| Fraction No. 1& 2 | Low response |
| Fraction No. 3& 4 | 24.465 |
| Fraction No. 5&6 | 25.362 |
| Fraction No. 7&8 | 26.185 |
| Fraction No. 11&12 | 27.890 |
| Fraction No. 15&16 | 29.582 |
| Fraction No. 19 & 20 | 31.095 |
| Fraction No. 23 & 24 | 33.054 |
| Fraction No. 27 &28 | 36.271 |

TABLE 3

Batch No. 3

| Fraction No. | Retention time (minutes) |
| --- | --- |
| Fraction No. 1& 2 | Low response |
| Fraction No. 3& 4 | 24.405 |
| Fraction No. 5&6 | 25.262 |
| Fraction No. 7&8 | 26.158 |
| Fraction No. 11&12 | 27.899 |
| Fraction No. 15&16 | 29.552 |
| Fraction No. 19 & 20 | 31.128 |
| Fraction No. 23 & 24 | 32.901 |
| Fraction No. 27 &28 | 36.223 |

The solution (60 mL) from each pooled fractions (Fractions 3 & 4 to Fractions 19 & 20) are poured in to the Centrifugal CutOff membrane (CutOff membrane of 5 KDa from GE Amersham Life science) and centrifuged at 25° C. and 3000 RPM of speed for 60 minutes till the volume concentrated to 20 mL. Milli Q water (20 mL) is added to the retentate side of the tube for further washing and again centrifuged until 20 mL removal in permeate side. The retentate solution from each of the membrane tube was collected separately. The concentrated solutions are lyophilized individually to afford 150 mg, 187 mg, 292 mg, 537 mg, 580 mg, and 277 mg of the title compound. Confirmation of molecular weight of the markers of the present application by MALDI (Matrix-Assisted Laser Desorption/Ionization) is given below:

TABLE 4

| S. No. | Fraction No | Molecular weight (Daltons) | Molar fraction | | | |
|---|---|---|---|---|---|---|
| | | | Glutamic acid | Alanine | Lysine | Tyrosine |
| 1 | Fraction No. 3 & 4 | 23.731  14600 | — | — | — | — |
| 2 | Fraction No. 5 & 6 | 24.723  12000 | 0.147 | 0.465 | 0.083 | 0.305 |
| 3 | Fraction No. 7 & 8 | 25.764  9600 | 0.153 | 0.476 | 0.084 | 0.287 |
| 4 | Fraction No. 11&12 | 27.564  6614 | 0.153 | 0.472 | 0.090 | 0.284 |
| 5 | Fraction No. 15 &16 | 29.268  4460 | 0.130 | 0.444 | 0.094 | 0.332 |
| 6 | Fraction No. 19 & 20 | 30.833  3600 | 0.147 | 0.437 | 0.116 | 0.300 |

Example 3

Superose™ 12 Column Calibration with Molecular Weight Markers of the Present Application.

Molecular weight markers that are prepared according to the procedure given in Example 1 above and a glatiramer acetate preparation are expected to demonstrate a similar correlation between retention time (RT) and log molecular weight. The molecular weight markers of the present application are chromatographed on Superose™ 12 column. The peak retention time for each of the markers is recorded. The linear correlation between Log Molecular Weight (MW) and the Retention Time (RT) is calculated as follows:

$$Log\ MW = A + B \times RT$$

where MW is the molecular weight, RT is the retention time, A and B, respectively, are the intercept and the slope of the calculated regression function.

| Molecular weight marker | Peak RT | Molecular weight (MW) | Log MW |
|---|---|---|---|
| 1 | 23.124 | 16833 Daltons | 4.22162 |
| 2 | 26.44 | 8908 Daltons | 3.94978 |
| 3 | 29.281 | 5006 Daltons | 3.699491 |
| 4 | 30.909 | 3709 Daltons | 3.569257 |
| Intercept (A) | | | 6.18943 |
| Slope (B) | | | −0.08485 |
| $r^2$ | | | 0.9998 |

In the similar manner, molecular weight markers that are prepared according to the procedure given in Example 2 above and a glatiramer acetate preparation are expected to demonstrate a similar correlation between retention time (RT) and log molecular weight. The molecular weight markers of the present application are chromatographed on Superose™ 12 column. The peak retention time for each of the markers is recorded. The linear correlation between Log Molecular Weight (MW) and the Retention Time (RT) is calculated as follows:

$$Log\ MW = A + B \times RT$$

where MW is the molecular weight, RT is the retention time, A and B, respectively, are the intercept and the slope of the calculated regression function.

| Molecular weight marker | Peak RT | Molecular weight (MW) | Log MW |
|---|---|---|---|
| 1 | 23.731 | 14600 | 4.1644 |
| 2 | 24.723 | 12000 | 4.0792 |
| 3 | 25.764 | 9600 | 3.9823 |
| 4 | 27.564 | 6614 | 3.8205 |
| 5 | 29.268 | 4460 | 3.6493 |
| 6 | 30.833 | 3600 | 3.5563 |
| Intercept (A) | | | 6.2585 |
| Slope (B) | | | −0.0883 |
| $r^2$ | | | 0.997 |

Before utilizing these markers for determining the molecular weight of Copaxone® or any other pharmaceutical composition consisting of glatiramer acetate, it is essential to establish a structural correlation between the markers and glatiramer acetate. The CD (Circular Dichroism) profile of the molecular weight markers that are prepared according to the procedure given in Example 1 above were compared against Copaxone® and the two profiles were found to be similar, indicating their structural homogeneity.

The Superose™-12 column pre-calibrated in the above manner was then used to determine the molecular weight of Copaxone® lots of innovator and different batch samples glatiramer acetate. The data in the table below shows that the results are well within the specified limits of 5 to 9KDa proposed for Copaxone®.

| S. No. | Sample | Molecular weight |
|---|---|---|
| 1 | Copaxone ® | 7797 Daltons |
| 2 | glatiramer acetate Batch 1 | 6262 Daltons |
| 3 | glatiramer acetate Batch 2 | 6636 Daltons |
| 4 | glatiramer acetate Batch 3 | 6923 Daltons |

Throughout this application, various publications are referenced. The disclosures of these publications in their entireties are hereby incorporated by reference into this application in order to more fully describe the state of the art as known to those skilled therein as of the date of the invention described and claimed herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A method of determining the peak average molecular weight of glatiramer acetate, wherein the method comprises providing molecular weight markers that comprise polypeptides having an amino acid composition corresponding to glatiramer acetate and a peak average molecular weight between about 2,000 Daltons and about 40,000 Daltons as determined by gel permeation chromatography and wherein said polypeptides have no predetermined amino acid sequence and using said polypeptides to determine the peak average molecular weight of glatiramer acetate.

2. The method of claim 1, wherein the peak average molecular weight is between about 2,000 Daltons and about 20,000 Daltons.

3. The method of claim 1, wherein the peak average molecular weight is between about 2,000 Daltons and about 15,000 Daltons.

4. The method of claim 1, wherein the peak average molecular weight is between about 2,000 Daltons and about 10,000 Daltons.

5. The method of claim 1, wherein the polypeptides consist essentially of the amino acids alanine, glutamic acid, tyrosine, and lysine in molar fractions of from about 0.38 to about 0.50 alanine, from about 0.13 to about 0.15 glutamic acid, from about 0.08 to about 0.10 tyrosine, and from about 0.3 to about 0.4 lysine.

6. A process for preparing the molecular weight markers of claim 1, comprising:
   (a) fractionating the polypeptides in a gel permeation chromatography (GPC) column;
   (b) passing the fractions collected in step (a) through molecular weight cut-off membranes;
   (c) isolating the molecular weight markers by lyophilizing the fractions collected from step (b); and
   (d) using the molecular weight markers of step (c) for determining a peak average molecular weight of glatiramer or a pharmaceutically acceptable salt thereof, by subjecting the glatiramer or pharmaceutically acceptable salt thereof to chromatography on a chromatographic column so as to determine an average molecular weight of a glatiramer or a pharmaceutically acceptable salt thereof, wherein the chromatography column is calibrated by using a plurality of said molecular weight markers having no predetermined amino acid sequence.

7. The process of claim 6, wherein a chromatography media for the gel permeation chromatography (GPC) column of step (a) includes a composite medium based on highly cross-linked porous agarose particles to which dextran have been covalently bonded, an allyl dextran cross-linked with N, N'-methylene bisacrylamide, a medium with high physical and chemical stability based on highly cross-linked porous agarose particles, or a dextran cross-linked with epichlorohydrin.

8. The process of claim 6, wherein the molecular cut-off membranes used in step (b) range from 1 KDa to 10 KDa, 1 KDa to 20 KDa, or 1 KDa to 30 KDa.

9. The method according to claim 6, wherein a molecular weight marker 1 has a peak average molecular weight of about 16833 Daltons.

10. The method according to claim 6, wherein a molecular weight marker 2 has a peak average molecular weight of about 8908 Daltons.

11. The method according to claim 6, wherein a molecular weight marker 3 has a peak average molecular weight of about 5006 Daltons.

12. The method according to claim 6, wherein a molecular weight marker 4 has a peak average molecular weight of about 3709 Daltons.

13. A process of calibration of a gel permeation chromatography column which process comprises passing a plurality of molecular weight markers that comprise polypeptides through gel permeation chromatography, wherein the polypeptides have an amino acid composition corresponding to glatiramer acetate and a peak average molecular weight between about 2,000 Daltons and about 40,000 Daltons and wherein said polypeptides have no predetermined amino acid sequence.

14. A process for preparation of glatiramer acetate comprising subjecting glatiramer or a pharmaceutically acceptable salt thereof to chromatography on a chromatographic column so as to determine a peak average molecular weight of the glatiramer or a pharmaceutically acceptable salt thereof, wherein the chromatography column is calibrated by using a plurality of molecular weight markers having a peak average molecular weight between about 2,000 Daltons and about 40,000 Daltons as determined by gel permeation chromatography and having no predetermined amino acid sequence.

* * * * *